US011642324B1

United States Patent
Agha et al.

(10) Patent No.: US 11,642,324 B1
(45) Date of Patent: May 9, 2023

(54) TOPICAL TRANEXAMIC ACID COMPOSITIONS AND METHODS OF USE THEREOF

(71) Applicant: Bio 54, LLC, Chapel Hill, NC (US)

(72) Inventors: Bushra Agha, Chapel Hill, NC (US); Douglas Edward Schoelzel, Durham, NC (US)

(73) Assignee: Bio 54, LLC, Chapel Hill, NC (US)

( * ) Notice: Subject to any disclaimer, the term of this patent is extended or adjusted under 35 U.S.C. 154(b) by 0 days.

(21) Appl. No.: 17/970,933

(22) Filed: Oct. 21, 2022

Related U.S. Application Data

(60) Provisional application No. 63/315,113, filed on Mar. 1, 2022.

(51) Int. Cl.
| | | |
|---|---|---|
| *A61K 31/165* | (2006.01) | |
| *A61K 47/12* | (2006.01) | |
| *A61K 47/38* | (2006.01) | |
| *A61K 9/00* | (2006.01) | |
| *A61K 31/195* | (2006.01) | |

(52) U.S. Cl.
CPC .......... *A61K 31/165* (2013.01); *A61K 9/0014* (2013.01); *A61K 31/195* (2013.01); *A61K 47/12* (2013.01); *A61K 47/38* (2013.01)

(58) Field of Classification Search
CPC .. A61K 31/165; A61K 9/0014; A61K 31/195; A61K 47/12; A61K 47/38
See application file for complete search history.

(56) References Cited

U.S. PATENT DOCUMENTS

| | | | |
|---|---|---|---|
| 3,639,626 A | 2/1972 | Nagasawa et al. | |
| 3,950,405 A | 4/1976 | Okano et al. | |
| 4,895,559 A | 1/1990 | Shippert | |
| 4,925,327 A | 5/1990 | Wirt | |
| 5,209,251 A | 5/1993 | Curtis et al. | |
| 5,288,159 A | 2/1994 | Wirt | |
| 5,308,180 A | 5/1994 | Pournoor et al. | |
| 5,405,360 A | 4/1995 | Tovey | |
| 5,445,462 A | 8/1995 | Johnson et al. | |
| 6,056,970 A | 5/2000 | Greenawalt et al. | |
| 6,786,883 B2 | 9/2004 | Shippert | |
| 6,991,394 B2 | 1/2006 | Tufts et al. | |
| 7,015,194 B2 | 3/2006 | Kjalke | |
| 7,108,706 B2 | 9/2006 | Hogle | |
| 7,202,065 B2 | 4/2007 | Romisch et al. | |
| 7,449,446 B2 | 11/2008 | Elg | |
| 7,465,460 B1 * | 12/2008 | Gross | A61K 8/365 514/159 |
| 7,531,318 B2 | 5/2009 | Srivastava et al. | |
| 7,674,250 B2 | 3/2010 | Freyman et al. | |
| 7,799,048 B2 | 9/2010 | Hudson et al. | |
| 7,845,536 B2 | 12/2010 | Viola et al. | |
| 7,887,837 B2 | 2/2011 | Takeoka et al. | |
| 7,931,637 B2 | 4/2011 | Vournakis et al. | |
| 7,947,739 B2 | 5/2011 | Moore et al. | |
| 8,022,106 B2 | 9/2011 | Moore et al. | |
| 8,137,375 B2 | 3/2012 | Hudson et al. | |
| 8,152,750 B2 | 4/2012 | Vournakis et al. | |
| 8,252,302 B2 | 8/2012 | Macdonald | |
| 8,257,701 B2 | 9/2012 | Orbe et al. | |
| 8,273,795 B2 | 9/2012 | Moore et al. | |
| 8,487,005 B2 | 7/2013 | Moore et al. | |
| 8,647,650 B2 | 2/2014 | Miyamoto et al. | |
| 8,674,074 B2 | 3/2014 | Ostergaard | |
| 8,697,747 B2 | 4/2014 | Nielsen et al. | |
| 8,758,785 B2 | 6/2014 | Miyamoto et al. | |
| 8,766,964 B2 | 7/2014 | Yamamoto et al. | |
| 8,784,876 B2 | 7/2014 | Huey et al. | |
| 8,791,160 B2 | 7/2014 | Moore et al. | |
| 8,802,083 B2 | 8/2014 | Vournakis et al. | |
| 8,802,362 B2 | 8/2014 | Grippi et al. | |
| 8,809,394 B2 | 8/2014 | Moore et al. | |
| 8,835,408 B2 | 9/2014 | Vournakis et al. | |
| 8,858,593 B2 | 10/2014 | Kerber | |
| 8,858,969 B2 | 10/2014 | Pahari et al. | |
| 8,956,065 B2 | 2/2015 | Froimson | |
| 8,957,113 B2 | 2/2015 | Moore et al. | |
| 8,968,777 B2 | 3/2015 | Heasley et al. | |
| 8,992,453 B2 | 3/2015 | Vournakis et al. | |
| 9,060,939 B2 | 6/2015 | Moore et al. | |
| 9,301,936 B2 | 4/2016 | Buderer et al. | |
| 9,320,653 B2 | 4/2016 | Vournakis et al. | |
| 9,345,651 B2 | 5/2016 | Kuromiya et al. | |

(Continued)

FOREIGN PATENT DOCUMENTS

| | | |
|---|---|---|
| CN | 103565743 B | 6/2016 |
| CN | 104490762 B | 11/2017 |

(Continued)

OTHER PUBLICATIONS

Tranexamic acid, DermNet. Retrieved from the interneton Jan. 30, 2023, https://dermnetnz.org/topics/tranexamic-acid. Published Aug. 2018. (Year: 2018).*

Convert mPa-s to cps-Conversion of Measurement Units, Convert Units. Retrieved from the internet on Jan. 30, 2023, https://www.convertunits.com/from/mPa-s/to/cps. (Year: 2023).*

Hapgood. Hydroxyethyl Cellulose. Retrieved from the Internet on Jan. 30, 2023, https://file.wuxuwang.com/hpe/HPE6/HPE6_138.pdf. Published Feb. 3, 2009. (Year: 2009).*

Translation of CN 103565743. Retrieved from Espacenet on Jan. 30, 2023, https://worldwide.espacenet.com/patent/search/family/050039026/publication/CN103565743A?q=cn103565743. Published 2014 (Year: 2014).*

(Continued)

*Primary Examiner* — Brandon J Fetterolf
*Assistant Examiner* — Lauren Wells
(74) *Attorney, Agent, or Firm* — Cooley LLP

(57) ABSTRACT

The present disclosure relates to pharmaceutical compositions of tranexamic acid and methods of using the compositions. The pharmaceutical compositions of the present disclosure are stable and suitable for topical application.

25 Claims, No Drawings

(56) References Cited

U.S. PATENT DOCUMENTS

| | | | |
|---|---|---|---|
| 9,387,178 B2 | 7/2016 | Joshi et al. |
| 9,408,913 B2 | 8/2016 | Wuollett et al. |
| 9,526,738 B2 | 12/2016 | Stasko et al. |
| 9,526,746 B2 | 12/2016 | Kemp et al. |
| 9,533,069 B2 | 1/2017 | Larsen et al. |
| 9,623,223 B2 | 4/2017 | Steinbaugh et al. |
| 9,717,821 B2 | 8/2017 | Schutte et al. |
| 9,821,022 B2 | 11/2017 | Norchi et al. |
| 9,839,716 B1 | 12/2017 | Nowakowski |
| 9,889,154 B2 | 2/2018 | Basadonna et al. |
| 9,950,091 B2 | 4/2018 | Mousa et al. |
| 10,118,930 B2 | 11/2018 | Ellermann et al. |
| 10,195,088 B2 | 2/2019 | Clayborne et al. |
| 10,239,342 B2 | 3/2019 | Fehlmann et al. |
| 10,292,955 B2 | 5/2019 | Lee et al. |
| 10,376,610 B2 | 8/2019 | Ertan |
| 10,407,488 B2 | 9/2019 | Griffin et al. |
| 10,420,864 B2 | 9/2019 | Pulapura et al. |
| 10,478,851 B2 | 11/2019 | Ettlin |
| 10,596,360 B2 | 3/2020 | Clarke |
| 10,668,071 B2 | 6/2020 | Ha et al. |
| 10,695,300 B2 | 6/2020 | Lee |
| 10,765,782 B2 | 9/2020 | Pulapura et al. |
| 10,800,905 B2 | 10/2020 | Delli-Santi et al. |
| 10,881,803 B2 | 1/2021 | McClellan et al. |
| 10,919,073 B2 | 2/2021 | Phipps et al. |
| 10,933,174 B2 | 3/2021 | Pulapura et al. |
| 10,980,676 B2 | 4/2021 | Clayborne et al. |
| 10,980,740 B2 | 4/2021 | Rangabhatla et al. |
| 11,007,218 B2 | 5/2021 | Basadonna et al. |
| 11,484,907 B2 | 11/2022 | Hiemer et al. |
| 2002/0176849 A1 | 11/2002 | Slepian |
| 2002/0192271 A1 | 12/2002 | Hedner et al. |
| 2003/0008831 A1 | 1/2003 | Yang et al. |
| 2003/0105483 A1 | 6/2003 | Hudson et al. |
| 2005/0054967 A1 | 3/2005 | Ashe et al. |
| 2005/0181978 A1 | 8/2005 | Rojkjaer et al. |
| 2005/0182011 A1 | 8/2005 | Olson et al. |
| 2005/0267014 A1 | 12/2005 | Rojkjaer |
| 2007/0038245 A1 | 2/2007 | Morris et al. |
| 2007/0218114 A1 | 9/2007 | Duggan et al. |
| 2007/0255238 A1 | 11/2007 | Cochrum et al. |
| 2008/0108926 A1 | 5/2008 | Voegele |
| 2008/0138387 A1 | 6/2008 | Machiraju |
| 2008/0193414 A1 | 8/2008 | Proudfoot et al. |
| 2010/0016880 A1 | 1/2010 | Ashenhurst |
| 2011/0060040 A1 | 3/2011 | Virsik et al. |
| 2011/0184060 A1 | 7/2011 | Harris Ma et al. |
| 2012/0022160 A1* | 1/2012 | Suzuki ............ A61Q 19/02 514/561 |
| 2012/0070470 A1 | 3/2012 | Pahari et al. |
| 2012/0302640 A1 | 11/2012 | Macalister |
| 2013/0029030 A1 | 1/2013 | Larsen |
| 2013/0330397 A1 | 12/2013 | Neas et al. |
| 2014/0220130 A1 | 8/2014 | Larsen et al. |
| 2015/0038406 A1 | 2/2015 | Buderer et al. |
| 2015/0119851 A1 | 4/2015 | Hoogenakker et al. |
| 2015/0289861 A1 | 10/2015 | Macphee et al. |
| 2015/0320982 A1 | 11/2015 | Massicotte |
| 2015/0366798 A1 | 12/2015 | Lozinsky et al. |
| 2016/0000823 A1 | 1/2016 | Emanuele et al. |
| 2016/0000863 A1 | 1/2016 | Rodr Guez Ferndez-Alba et al. |
| 2016/0206580 A1 | 7/2016 | Los et al. |
| 2016/0220799 A1 | 8/2016 | Tarlow et al. |
| 2016/0346239 A1 | 12/2016 | Korobov |
| 2017/0135926 A1 | 5/2017 | Hu et al. |
| 2017/0319755 A1 | 11/2017 | Pulapura et al. |
| 2018/0064780 A1 | 3/2018 | Ingber et al. |
| 2018/0093010 A1 | 4/2018 | Nur et al. |
| 2018/0093043 A1 | 4/2018 | McClellan et al. |
| 2018/0116986 A1 | 5/2018 | Joshi et al. |
| 2018/0125721 A1 | 5/2018 | Hoggarth et al. |
| 2018/0140302 A1 | 5/2018 | Pai et al. |
| 2018/0193874 A1 | 7/2018 | Pozanc et al. |
| 2018/0207413 A1 | 7/2018 | Skakoon et al. |
| 2018/0236123 A1 | 8/2018 | Manoryk et al. |
| 2018/0243505 A1 | 8/2018 | Genosar |
| 2018/0264243 A1 | 9/2018 | Cordoba et al. |
| 2018/0271898 A1 | 9/2018 | Basadonna et al. |
| 2019/0184052 A1 | 6/2019 | Ilan et al. |
| 2019/0192564 A1 | 6/2019 | Hijazi et al. |
| 2019/0224121 A1 | 7/2019 | Erstad et al. |
| 2020/0046663 A1 | 2/2020 | Murdock et al. |
| 2020/0121871 A1 | 4/2020 | Genosar |
| 2020/0253874 A1 | 8/2020 | Vadelund et al. |
| 2020/0289415 A1 | 9/2020 | Kelm et al. |
| 2020/0360055 A1 | 11/2020 | Hong et al. |
| 2021/0001023 A1 | 1/2021 | Hijazi et al. |
| 2021/0008243 A1 | 1/2021 | Ericson |
| 2021/0046121 A1 | 2/2021 | Moskowitz et al. |
| 2021/0228478 A1 | 7/2021 | Rangabhatla |
| 2021/0386984 A1 | 12/2021 | Skakoon et al. |
| 2022/0062058 A1 | 3/2022 | Manasco et al. |
| 2022/0249292 A1 | 8/2022 | Manasco et al. |

FOREIGN PATENT DOCUMENTS

| | | |
|---|---|---|
| EP | 0711175 B1 | 8/2001 |
| JP | 2906270 B2 | 6/1999 |
| JP | 2001017461 A | 1/2001 |
| JP | 2005029529 A | 2/2005 |
| JP | 6370094 B2 | 8/2018 |
| JP | 6830735 B2 | 2/2021 |
| JP | 2021167284 A | 10/2021 |
| KR | 20160128888 A | 11/2016 |
| KR | 20210115591 A | 9/2021 |
| NZ | 709379 A | 3/2017 |
| TW | 200841889 A | 11/2008 |
| WO | WO-0009018 A1 | 2/2000 |
| WO | WO-2006114338 A1 | 11/2006 |
| WO | WO-2008050173 A1 | 5/2008 |
| WO | WO-2013093164 A1 | 6/2013 |
| WO | WO-2014209389 A1 | 12/2014 |
| WO | WO-2015107139 A1 | 7/2015 |
| WO | WO-2016178053 A1 | 11/2016 |
| WO | WO-2017007917 A1 | 1/2017 |
| WO | WO-2018197946 A1 | 11/2018 |
| WO | WO-2018232277 A1 | 12/2018 |
| WO | WO-2019219130 A1 | 11/2019 |
| WO | WO-2019230579 A1 | 12/2019 |
| WO | WO-2020046769 A1 | 3/2020 |
| WO | WO-2020176507 A1 | 9/2020 |
| WO | WO-2020248010 A1 | 12/2020 |
| WO | WO-2021207698 A1 | 10/2021 |
| WO | WO-2021216494 A1 | 10/2021 |
| WO | WO 2022-040450 A1 | 2/2022 |

OTHER PUBLICATIONS

Sivr et al. Decontamination of Cosmetic Prducts and Raw Materials by Gamma Irradiation, FABAD J. Pharm. Sci., 31, 198-209, 2006. (Year: 2006).*

Translation of JP2007131547. Retrieved from Espaceneton Jan. 30, 2023, https://worldwide.espacenet.com/patent/search/family/038153501/publication/JP2007131547A?q=jp2007131547. Published 2007. (Year: 2007).*

Amini, et al., "Topical Tranexamic Acid versus Phenylephrine-lidocaine for the Treatment of Anterior Epistaxis in Patients Taking Aspirin or Clopidogrel; a Randomized Clinical Trial," Archives in Academic Emergency Medicine, 2021, 9(1):e6:1-7.

Ausen, et al., "Serum Concentrations and Pharmacokinetics of Tranexamic Acid after Two Means of Topical Administration in Massive Weight Loss Skin-Reducing Surgery," Cosmetic, Jun. 2019, 143(6):1169e-1178e.

Baylis, et al., "Self-propelled dressings containing thrombin and tranexamic acid improve short-term survival in a swine model of lethal junctional hemorrhage," Shock, Sep. 2016, 46(3):123-128.

Boccio, et al., "Topical Tranexamic Acid for Hemostasis of an Oral Bleed in a Patient on a Direct Oral Anticoagulant," Clinical Practice and Cases in Emergency Medicine, May 2020, IV(2):146-149.

(56) References Cited

OTHER PUBLICATIONS

Borea, et al., "Tranexamic acid as a mouthwash in anticoagulant-treated patients undergoing oral surgery," Oral Surg. Oral Med. Oral Pathol., 1993, 75:29-31.
Burns, "Case Report: Topical Tranexamic Acid as Novel Treatment of Refractory Bleeding After Excisional Cervical Procedure [27G]," Saturday Posters, Obstetrics & Gynecology, 2018, 82S.
Carter, et al., "Current concepts of the management of dental extractions for patients taking warfarin," Australian Dental Journal, 2003, 48(2):89-96.
Carter, et al., "Tranexamic acid mouthwash—A prospective randomized study of a 2-day regimen vs 5-day regimen to prevent postoperative bleeding in anticoagulated patients requiring dental extractions," Int. J. Oral Maxillofac. Surg., 2003, 32:504-507.
Carter, et al., "Tranexamic Acid Mouthwash Versus Autologous Fibrin Glue in Patients Taking Warfarin Undergoing Dental Extractions: A Randomized Prospective Clinical Study," J. Oral Maxillofac Surg, 2003, 61:1432-1435.
ClinicalTrials.gov Identifier: NCT02918201, The Effect of Topical Tranexamic Acid on Postoperative Bleeding from Superficial Wounds, last update posted Feb. 1, 2021, 1-8.
Coetzee, "The use of topical crushed tranexamic acid tablets to control bleeding after dental surgery and from skin ulcers in haemophilia," Haemophilia, 2017, 13:443-444.
Condoret, et al., "Industrialized of a supercritical $CO_2$ process for oxidation of cellulose," Universite de Toulouse, Laboratoire de Génie Chimique, INP, CNRS, UPS, Tououse, France, 2015, 1-4.
Cyklokapron® (tranexamic acid) injection, for intravenous use, Initial U.S. Approval: 1986, revised Mar. 2021, 1-10.
Eikebrokk, et al., "Cytotoxicity and effect on wound re-epithelialization after topical administration of tranexamic acid," BJS Open, 2019, 3:840-851.
Glineur, et al., "A randomized, controlled trial of Veriset™ hemostatic patch in halting cardiovascular bleeding," Medical Devices: Evidence and Research, 2018, 11:65-75.
Hydrasorb® Hydrophilic Urethane Foam Product Data Sheet, Carwild Corp, Jun. 2014, 1 page.
Hydrophilic SAQ, Product Data Sheet, Woodbridge INOAC Technical Products, revised Aug. 2017, 1 page.
International Search Report and Written Opinion issued in PCT/US2021/026714, dated Jul. 28, 2021, 1-9.
International Search Report and Written Opinion issued in PCT/US2021/053641, dated Dec. 29, 2021, 1-23.
Joseph, et al., "Does Oral or Topical Tranexamic Acid Control Bleeding from Epistaxis?" Annals of Emergency Medicine, Aug. 2019, 74(2):300-302.
Joseph, et al., "Tranexamic acid for patients with nasal haemorrhage (epistaxis)," Cochrane Database of Systematic Reviews, 2018, 12(CD004328):1-4.
Ker, et al., "Topical application of tranexamic acid for the reduction of bleeding (Review)," Cochrane Database of Systematic Reviews, 2013, 7(CD010562):1-65.
Liu, et al., "Topical Metered-dosing Dispenser Performance Evaluation," International Journal of Pharmaceutical Compounding, 2016, 20(3):239-246.
LYSTEDA™ (tranexamic acid) Tablets, Initial U.S. Approval: 1986, revised: Oct. 2013, Reference ID: 3383847, 1-20.
Montroy, et al., "The efficacy and safety of topical tranexamic acid: A systematic review and meta-analysis," Transfusion Medicine Reviews, 2018, 1-14.
Morgenstern, "NoPAC: No benefit from TXA in epistaxis, TXA for Epistaxis," First10EM, 1-9.
NHS, "Use of Topical Tranexamic Acid to control surface bleeding from the fungating wounds in the skin," East Lancashire Health Economy Medicines Management Board, review date Nov. 30, 2020, 1 page.
Nikoyan, et al., "Epistaxis and hemostatic devices," Oral Maxillofacial Surg. Clin. N. Am., 2012, 24:219-228.
Noble, et al., "Case report: use of topical tranexamic acid to stop localised bleeding," Emerg. Med. J., 2013, 30:509-510.
Non-Final Office Action for U.S. Appl. No. 17/522,736, dated Jun. 2, 2022, 20 pages.
Non-Final Office Action for U.S. Appl. No. 17/522,736, dated Oct. 17, 2022, 14 pages.
Non-Final Office Action for U.S. Appl. No. 17/728,894, dated Jul. 14, 2022, 23 pages.
Nuvvula, et al., "Efficacy of tranexamic acid mouthwash as an alternative for factor replacement in gingival bleeding during dental scaling in cases of hemophilia: A randomized clinical trial," Contemp Clin. Dent., Jan.-Mar. 2014, 5(1):49-53.
Patatanian, et al., "Hemostatic Mouthwashes in Anticoagulated Patients Undergoing Dental Extraction," The Annals of Pharmacotherapy, Dec. 2006, 40:2205-2210.
Product ID: 4-010-XX, Technical Data Sheet, Superior Felt & Filtration, 2018, 1 page.
PrTranexamic Acid Injection, USP. Product Monograph, 100 mg / ml Tranexamic acid injection USP, Sterile Solution Antifibrinolytic agent, Baxter Corporation, Sep. 17, 2020, Control No. 229119, 1-21.
PVA Expandacell® foam for epistaxis management after trauma or surgery, Rhino Rocket® Nasal Packing, Summit Medical, Shipped Medical, https://summitmedicalusa.com/rhinology/rhinorocket-nasal-packing/, retrieved on Jun. 16, 2021, 1 page.
Question: Can tranexamic acid be applied topically to a bleeding wound? Palliative Meds Info, Dec. 2018, 1-2.
Rapid Rhino Epistaxis Products: Inflatable tamponade designed to create a fast, single treatment solution with a low-profile and self-lubricating properties, Smith & Nephew, Inc., 2015, 1-4.
Recothrom, Thrombin topical (Recombinant) Package Insert, 2008 https://www.fda.gov/media/75321/download, 18 pages.
Reuben, et al., "The Use of Tranexamic Acid to Reduce the Need for Nasal Packing in Epistaxis (NoPAC): Randomized Controlled Trial," Annals of Emergency Medicine, 2021, 1-10.
Reversal strategies DOAC bleeding—UptoDate, "Direct oral anticoagulant-associated bleeding reversal strategies," UptoDate, Inc., 2021, https://www.uptodate.com/contents/image?imageKey=HEME/96230, 1-2.
Siegal, et al., "How I treat target-specific oral anticoagulant-associated bleeding," Blood, Feb. 2014, 123(8):1152-1158 (7 pages total).
Siegel, et al., "Vorinostat in combination with lenalidomide and dexamethasone in patients with relapsed or refractory multiple myeloma," Blood Cancer Journal, 2014, 4:e182:1-6.
Sm32h, Product Data Sheet, Woodbridge INOAC Technical Products, revised Aug. 2017, 1 page.
Swaminathan, "Topical TXA in Epistaxis," Rebel EM, Dec. 7, 2017, https://rebelem.com/topical-txa-in-epistaxis/, 1-13.
Tranexamic Acid in Sodium Chloride injection, for intravenous use. Initial U.S. Approval: 1986, Revised Apr. 2019, Reference ID: 4419268, 1-8.
UNC Medical Center Guideline, "Tranexamic Acid in Adult Emergency Department Patients," 2019, 1-4.
Utkewicz, et al., "Epistaxis Complicated by Rivaroxaban Managed with Topical Tranexamic Acid: Case Report and Literature Review," American Journal of Emergency Medicine, 2015, 1-11.
Whitworth, et al., "Comparative effectiveness of topically administered tranexamic acid versus topical oxymetazoline spray for achieving hemostasis in epistaxis," The Journal of Emergency Medicine, 2019, 1-6.
Whitworth, et al., "Data on the hemostasis in epistaxis with Topically Administered TXA Versus Topical Oxymetazoline Spray," Data in brief, 2020, 29(105283), 1-4.
Wound Home Skills Kit: Lacerations & Abrasions, Surgical Patient Education Program, American College of Surgeons Division of Education, Oct. 23, 2017, 1-41.
Zahed, et al., "A new and rapid method for epistaxis treatment using injectable form of tranexamic acid topically: a randomized controlled trial," American Journal of Emergency Medicine, 2013, 31:1389-1392.
Zahed, et al., "CME Information: Topical Tranexamic Acid Compared with Anterior Nasal Packing for Treatment of Epistaxis in Patients taking Antiplatelet Drugs: Randomized Controlled Trial," Society for Academic Emergency Medicine, 2017, 261-266.

(56) References Cited

OTHER PUBLICATIONS

Zirk, et al., "Supportive topical tranexamic acid application for hemostasis in oral bleeding events—retrospective cohort study of 542 patients," Journal of Cranio-Maxillo-Facial Surgery, 2018, doi: 10.1016/j.jcms.2018.03.009, 1-25.

* cited by examiner

TOPICAL TRANEXAMIC ACID COMPOSITIONS AND METHODS OF USE THEREOF

CROSS-REFERENCE TO RELATED APPLICATIONS

This application claims the benefit of priority to U.S. Provisional Application No. 63/315,113, filed Mar. 1, 2022, the contents of which are hereby incorporated by reference in their entirety herein

BACKGROUND

Tranexamic acid (TXA) is a synthetic lysine derivative with anti-fibrinolytic activity. LYSTEDA® is an FDA-approved, orally administered TXA tablet approved for the treatment of heavy menstrual bleeding in females of reproductive potential. CYKLOKAPRON® Injection is an FDA-approved Intravenous (IV) formulation indicated in patients with hemophilia for short-term use to reduce or prevent hemorrhage and reduce the need for replacement therapy during and following tooth extraction.

Orally and intravenously administered TXA provides systemic TXA exposure and, as such, associated systemic side effects (such as blood clots, seizures, and blurred vision). Additionally, systemic TXA does not concentrate its effect at the site of a wound or lesion. Thus, there is a need for TXA formulations that provide reduced bleeding while minimizing systemic exposure compared to orally or intravenously administered formulations.

The present disclosure provides TXA-containing compositions that carry an effective amount of TXA for topical use.

SUMMARY OF THE DISCLOSURE

The present disclosure provides tranexamic acid (TXA) compositions for use in pharmaceutical and cosmetic applications.

In one aspect, the present disclosure provides a topical aqueous composition for reducing bleeding. In embodiments, the compositions of the present disclosure contain TXA in a pharmaceutically acceptable aqueous vehicle and are suitable for topical administration.

In embodiments, the present disclosure provides stable compositions comprising a therapeutically effective amount of TXA and a viscosity modifying agent in a pharmaceutically acceptable aqueous vehicle. In embodiments, the viscosity modifying agent is hydroxyethyl cellulose.

In embodiments, the compositions of the present disclosure comprise about 200-300 mg/mL of TXA. In embodiments, the compositions of the present disclosure comprise about 200 mg/mL of TXA. In embodiments, the compositions of the present disclosure comprise about 300 mg/mL of TXA.

In embodiments, the viscosity of the composition is from about 1 to 2000 cps, wherein the viscosity is measured at 21° C. using a rotational viscosity method. In embodiments, the viscosity of the composition is from about 1 to 50 cps, wherein the viscosity is measured at 21° C. using a rotational viscosity method. In embodiments, the viscosity of the composition is from about 1 to 100 cps, wherein the viscosity is measured at 21° C. using a rotational viscosity method.

In embodiments, the composition further comprises a pH buffer agent. In embodiments, the pH buffer agent is sodium citrate and citric acid.

In embodiments, the composition has a pH value of about 3 to about 5. In embodiments, the pH of the composition is about 4.

In embodiments, the topical aqueous composition of TXA is sterile.

DETAILED DESCRIPTION

Definitions

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The term "about" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example, in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The term "aqueous" as used herein is a composition wherein the composition contains greater than 50% by weight of water. In embodiments, the aqueous compositions of the present disclosure contain greater than 75% by weight of water. In embodiments, the aqueous compositions of the present disclosure contain greater than 90% by weight of water.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent (such as TXA) from one organ, or portion of the body, to another organ or portion of the body.

The terms "effective amount" and "therapeutically effective amount" are used interchangeably in this disclosure and refer to an amount of a compound that, when administered to a patient, is capable of performing the intended result. For example, an effective amount of TXA in a composition is that amount that is required to reduce at least one symptom of a skin disease or bleeding in a patient. The actual amount that comprises the "effective amount" or "therapeutically effective amount" will vary depending on a number of conditions including, but not limited to, the severity of the disorder and the size and health of the patient, or the size of a wound to be treated. A skilled medical practitioner can readily determine the appropriate amount using methods known in the medical field.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Examples of inorganic acids include hydrochloric acid and sulfuric acid. Examples of organic acids include ethanesulfonic acid, benzenesulfonic acid, p-toluenesulfonic acid, straight-chain monocarboxylic acids (e.g., acetic acid and formic acid), polycarboxylic acids (e.g., citric acid and oxalic acid) and lactic acid. Suitable pharmaceutically acceptable alkali metal salts of free acids can be prepared from an inorganic base or an organic base. Examples of inorganic bases include the hydroxides, carbonates, and bicarbonates of ammonia, sodium, lithium, potassium, calcium, magnesium, aluminum, zinc and the like. Examples of organic bases include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; tromethamine, and the like. See, e.g., J. Pharm. Sci., 66: 1-19 (1977).

The term "preventing" as used herein with regard to a condition (such as scarring) refers to administration of a composition that reduces the frequency of, or delays the onset of, signs and/or symptoms of a condition in a subject relative to a subject which does not receive the composition. For example, the TXA compositions of the present disclosure may be used for preventing scarring in a patient in need thereof.

The term "treating" as used herein with regard to a patient, refers to improving at least one symptom of the patient's condition or disease. For example, a patient's epistaxis (nosebleed) is treated when, after administering a composition of the present disclosure, the rate of bleeding is reduced compared to prior to the administration. A patient's wound or external bleeding is treated when, after administering a composition of the present disclosure, the rate of bleeding is reduced compared to prior to the administration.

Tranexamic Acid Compositions

In embodiments, the present disclosure provides high concentration tranexamic acid (TXA) compositions that are suitable for topical administration. In embodiments, the viscosity of the compositions of the present disclosure provides TXA compositions is such that the composition resides on a wound or abnormal skin site for a prolonged period of time (e.g., at least about 10 minutes). In embodiments, the present disclosure provides TXA compositions that are stable (e.g., physically and chemically stable) upon storage (such as under ICH accelerated stability testing conditions).

In one aspect, the present disclosure provides a topical aqueous composition for reducing bleeding. In embodiments, the composition comprises about 50 mg/mL to about 500 mg/mL of TXA, e.g., about 50 mg/mL, about 100 mg/mL, about 150 mg/mL, about 200 mg/mL, about 250 mg/mL, about 300 mg/mL, about 350 mg/mL, about 400 mg/mL, about 450 mg/mL, or about 500 mg/mL including all values and ranges there between.

In embodiments, the composition comprises about 50 mg/mL to about 500 mg/mL of TXA, for example, about 50 mg/mL to about 480 mg/mL, about 50 mg/mL to about 450 mg/mL, about 50 mg/mL to about 430 mg/mL, about 50 mg/mL to about 400 mg/mL, about 50 mg/mL to about 380 mg/mL, about 50 mg/mL to about 350 mg/mL, about 50 mg/mL to about 330 mg/mL, about 50 mg/mL to about 300 mg/mL, about 50 mg/mL to about 280 mg/mL, about 50 mg/mL to about 250 mg/mL, about 50 mg/mL to about 230 mg/mL, about 50 mg/mL to about 200 mg/mL, about 50 mg/mL to about 180 mg/mL, about 50 mg/mL to about 150 mg/mL, about 50 mg/mL to about 130 mg/mL, about 50 mg/mL to about 100 mg/mL, about 100 mg/mL to about 500 mg/mL, about 100 mg/mL to about 480 mg/mL, about 100 mg/mL to about 450 mg/mL, about 100 mg/mL to about 430 mg/mL, about 100 mg/mL to about 400 mg/mL, about 100 mg/mL to about 380 mg/mL, about 100 mg/mL to about 350 mg/mL, about 100 mg/mL to about 330 mg/mL, about 100 mg/mL to about 300 mg/mL, about 100 mg/mL to about 280 mg/mL, about 100 mg/mL to about 250 mg/mL, about 100 mg/mL to about 230 mg/mL, about 100 mg/mL to about 200 mg/mL, about 100 mg/mL to about 180 mg/mL, about 100 mg/mL to about 150 mg/mL, about 100 mg/mL to about 130 mg/mL, about 150 mg/mL to about 500 mg/mL, about 150 mg/mL to about 480 mg/mL, about 150 mg/mL to about 450 mg/mL, about 150 mg/mL to about 430 mg/mL, about 150 mg/mL to about 400 mg/mL, about 150 mg/mL to about 380 mg/mL, about 150 mg/mL to about 350 mg/mL, about 150 mg/mL to about 330 mg/mL, about 150 mg/mL to about 300 mg/mL, about 150 mg/mL to about 280 mg/mL, about 150 mg/mL to about 250 mg/mL, about 150 mg/mL to about 230 mg/mL, about 150 mg/mL to about 200 mg/mL, about 150 mg/mL to about 180 mg/mL, about 200 mg/mL to about 500 mg/mL, about 200 mg/mL to about 480 mg/mL, about 200 mg/mL to about 450 mg/mL, about 200 mg/mL to about 430 mg/mL, about 200 mg/mL to about 400 mg/mL, about 200 mg/mL to about 380 mg/mL, about 200 mg/mL to about 350 mg/mL, about 200 mg/mL to about 330 mg/mL, about 200 mg/mL to about 300 mg/mL, about 200 mg/mL to about 280 mg/mL, about 200 mg/mL to about 250 mg/mL, about 200 mg/mL to about 230 mg/mL, in a pharmaceutically acceptable aqueous vehicle.

In embodiments, the composition comprises about 50-350 mg/mL of TXA in a pharmaceutically acceptable aqueous vehicle. In embodiments, the composition comprises about 100-250 mg/mL of TXA in a pharmaceutically acceptable aqueous vehicle. In embodiments, the composition comprises about 50-350 mg/mL of TXA. In embodiments, the composition comprises about 100-300 mg/mL of TXA. In embodiments, the composition comprises about 120-250 mg/mL of TXA. In embodiments, the composition comprises about 150-200 mg/mL of TXA. In embodiments, the composition comprises about 200-500 mg/mL of TXA. In embodiments, the composition comprises about 200-400 mg/mL of TXA. In embodiments, the composition comprises about 200-300 mg/mL of TXA.

In embodiments, the composition comprises about 500 mg/mL of TXA. In embodiments, the composition comprises about 400 mg/mL of TXA. In embodiments, the composition comprises about 350 mg/mL of TXA. In embodiments, the composition comprises about 300 mg/mL of TXA. In embodiments, the composition comprises about 250 mg/mL of TXA. In embodiments, the composition comprises about 200 mg/mL of TXA. In embodiments, the composition comprises about 100 mg/mL of TXA. In embodiments, the composition comprises about 50 mg/mL of TXA.

In embodiments, the concentration of TXA is selected based on the type and severity of the patient's bleeding.

In embodiments, the composition comprises about 5% to about 45% by weight of TXA, e.g., about 5% by weight, about 10% by weight, about 15% by weight, about 20% by weight, about 25% by weight, about 30% by weight, about 35% by weight, about 40% by weight, or about 45% by weight, including all values and ranges there between. In embodiments, the composition comprises about 10-25% by weight of TXA in a pharmaceutically acceptable aqueous vehicle. In embodiments, the composition comprises about 5-35% by weight of TXA. In embodiments, the composition comprises about 10-30% by weight of TXA. In embodiments, the composition comprises about 12-25% by weight of TXA. In embodiments, the composition comprises about 12-40% by weight of TXA. In embodiments, the composition comprises about 15-20% by weight of TXA. In embodiments, the composition comprises about 15-40% by weight of TXA. In embodiments, the composition comprises about 20-50% by weight of TXA. In embodiments, the composition comprises about 50% by weight of TXA. In embodiments, the composition comprises about 40% by weight of TXA. In embodiments, the composition comprises about 35% by weight of TXA. In embodiments, the composition comprises about 30% by weight of TXA. In embodiments, the composition comprises about 20% by weight of TXA. In embodiments, the composition comprises about 10% by weight of TXA. In embodiments, the composition comprises about 50% by weight of TXA. In embodiments, the composition comprises about 18% by weight of TXA. In embodiments, the composition comprises about 27% by weight of TXA.

In embodiments, the composition is packaged in a suitable container. In embodiments, the volume of the composition is about 0.5 mL to about 30 mL, e.g., about 0.5 mL, about 1.0 mL, about 1.5 mL, about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, about 10.0 mL, about 10.5 mL, about 11.0 mL, about 11.5 mL, about 12.0 mL, about 12.5 mL, about 13.0 mL, about 13.5 mL, about 14.0 mL, about 14.5 mL, about 15.0 mL, about 15.5 mL, about 16.0 mL, about 16.5 mL, about 17.0 mL, about 17.5 mL, about 18.0 mL, about 18.5 mL, about 19.0 mL, about 19.5 mL, about 20.0 mL, about 21.0 mL, about 22.0 mL, about 23.0 mL, about 24.0 mL, about 25.0 mL, about 26.0 mL, about 27.0 mL, about 28.0 mL, about 29.0 mL, or about 30.0 mL, including all values and ranges there between.

In embodiments, the volume of the composition is about 2 mL to about 10 mL, e.g., about 2.0 mL, about 2.5 mL, about 3.0 mL, about 3.5 mL, about 4.0 mL, about 4.5 mL, about 5.0 mL, about 5.5 mL, about 6.0 mL, about 6.5 mL, about 7.0 mL, about 7.5 mL, about 8.0 mL, about 8.5 mL, about 9.0 mL, about 9.5 mL, or about 10 mL, including all values and ranges there between. In embodiments, the volume of the composition is about 10 mL. In embodiments, the volume of the composition is about 9 mL. In embodiments, the volume of the composition is about 8 mL. In embodiments, the volume of the composition is about 7 mL. In embodiments, the volume of the composition is about 6 mL. In embodiments, the volume of the composition is about 5 mL. In embodiments, the volume of the composition is about 4 mL. In embodiments, the volume of the composition is about 3 mL. In embodiments, the volume of the composition is about 2 mL.

In embodiments, the packaged composition comprises about 100 mg to about 5,000 mg of TXA, e.g., about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, about 3000 mg, about 3100 mg, about 3200 mg, about 3300 mg, about 3400 mg, about 3500 mg, about 3600 mg, about 3700 mg, about 3800 mg, about 3900 mg, about 4000 mg, about 4100 mg, about 4200 mg, about 4300 mg, about 4400 mg, about 4500 mg, about 4600 mg, about 4700 mg, about 4800 mg, about 4900 mg, or about 5000 mg, including all values and ranges there between.

In embodiments, the packaged composition comprises about 250 mg to about 2,000 mg of TXA, e.g., about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg about 1900 mg, about 1950 mg, or about 2000 mg, including all values and ranges there between.

In embodiments, the packaged composition comprises about 1000 mg to about 2,000 mg of TXA, e.g., about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg, including all values and ranges there between.

In embodiments, the composition of the present disclosure comprises tranexamic acid (TXA) at an effective concentration in a pharmaceutically acceptable aqueous vehicle and further comprises a pharmaceutically acceptable excipient, such as, for example, emulsifiers, wetting agents or fillers, such as, for example, the polyethylene glycols designated 200, 300, 400 and 600, or Carbowax designated 1000, 1500, 4000, 6000 and 10000. The amount and type of excipient added is in accordance with the particular requirements and is generally in the range of from approximately 0.0001 to approximately 90% by weight.

In embodiments, the compositions of the present disclosure further comprise a viscosity modifying agent. In embodiments, the viscosity agent is acacia, agar, alginic acid, aluminum monostearate, ammonium sulfate, attapulgite, bentonite, betadex sulfobutyl ether sodium, calcium alginate, calcium lactate, carbomers, carboxymethylcellulose calcium, carboxymethylcellulose sodium with microcrystalline cellulose, carrageenan, cellulose microcrystalline, carboxymethylcellulose sodium, ceratonia, ceresin, cetostearyl alcohol, cetyl palmitate, chitosan, colloidal silicon dioxide, corn syrup solids, cyclomethicone, dextrin, ethylcellulose, gelatin, gellan gum, glycerin, glyceryl behenate, glyceryl laurate, guar gum, hectorite, hydrogenated palm oil, hydrogenated vegetable oil type I, hydrophobic colloidal silica, bydroxyethyl cellulose, hydroxyethylmethyl cellulose, hydroxypropyl cellulose, hypromellose, magnesium aluminum silicate, maltodextrin, methylcellulose, microcrystalline cellulose, and carboxymethylcellulose sodium, modified starch, myristyl alcohol, octyldodecanol, pectin, polycarbophil, polydextrose, polyethylene glycol, polyethylene oxide, poly(methylvinyl ether/maleic anhydride), polyoxyethylene alkyl ethers, polyvinyl alcohol, potassium alginate, povidone, propylene glycol alginate, propylene glycol dilaurate, pullulan, saponite, sodium alginate, sodium chloride, starch, stearic acid, stearyl alcohol, sucrose, tragacanth, trehalose, or xanthan gum, or a mixture thereof.

In embodiments, the viscosity modifying agent is a polyol (such as, glycerol, glycerin, polyethylene glycol 300, polyethylene glycol 400, polysorbate 80, propylene glycol, and ethylene glycol), polyvinylpyrrolidone; a cellulose derivative (such hydroxypropyl methyl cellulose, carboxymethyl cellulose sodium, hydroxypropyl cellulose, hydroxyethyl cellulose, and methyl cellulose); a dextran (such as dextran 70); a water soluble protein (such as gelatin); a carbomer (such as carbomer 934P, carbomer 941, carbomer 940 and carbomer 974P); or a gum (such as HP-guar), or a mixture thereof.

In embodiments, the viscosity modifying agent is methylcellulose, carboxymethyl cellulose sodium (MV), carbomers, xanthan gum, poloxamer 407, carboxymethyl cellulose, methylcellulose 400 cp, pemulen TR-1, pemulen TR-2, hydroxyethyl cellulose, or a combination thereof.

In embodiments, the viscosity modifying agent is a hydrophobic oil. In embodiments, the viscosity modifying agent is a fatty alcohol, fatty acid, or a wax. In embodiments, the viscosity modifying agent is lauryl alcohol, myristyl alcohol, cetyl alcohol, stearyl alcohol, arachidyl alcohol, behenyl alcohol, tetracosanol, hexacosanol, octacosanol, triacontanol, tetratriacontanol; and wherein the fatty acid is selected from the group consisting of dodecanoic acid, tetradecanoic acid, hexadecanoic acid, heptadecanoic acid, octadecanoic acid, eicosanoic acid, docosanoic acid, tetracosanoic acid, hexacosanoic acid, heptacosanoic acid, octacosanoic acid, triacontanoic acid, dotriacontanoic acid, tritriacontanoic acid, tetratriacontanoic acid, pentatriacontanoic acid, plant wax, an animal wax, a petroleum derived wax, and a vegetable wax; or wherein the wax is selected from the group consisting of an albacer wax, an atlasene wax, a cardis wax, a ceramide, an alkyl-substituted aromatic compound, a naphthene-substituted aromatic compound, a beeswax, a carnauba wax, a chinese wax, a cotton wax, a bayberry wax, a carnauba wax, a castor wax, a cuban palm wax, a duroxon wax, an esparto wax, a fat wax, a flax wax, a fischer-tropsch wax, a fir wax, a flexo wax a flower wax, glyco waxes, a japan wax, a jojoba oil, a lanolin wax, a palm wax, a rice bran wax, a rice-oil wax, a shellac wax, a soy wax, an ucuhuba wax, a hydrogenated oil, a hydrogenated castor oil, a hydrogenated cottonseed oil, a hydrogenated jojoba oil, a mink wax, a mixture of saturated n- and isoalkanes, a montan wax, a naphthene, an ouricury wax, an oxazoline wax, an ozokerite, a paraffin wax, a paraffin 58-62° C. wax, paraffin 51-53° C. wax, paraffin 42-44° C. wax, a polyethylene wax, a PEG-6 beeswax, a polymekon wax, a retamo wax, a rezo wax, a sandy wax, a spent grain wax, a stearyl dimethicone, a sugarcane wax, or a synthetic mineral wax, or a mixture thereof.

In embodiments, the viscosity modifying agent is hydroxyethyl cellulose. In embodiments, the hydroxyethyl cellulose has a viscosity of about 400 cps to about 2000 cps (2% aqueous solution at 20° C.). In embodiments, the hydroxyethyl cellulose has a viscosity of about 800 cps to about 1500 cps (2% aqueous solution at 20° C.). In embodiments, the hydroxyethyl cellulose has a viscosity of about 4000 cps to about 7000 cps (2% aqueous solution at 20° C.). In embodiments, the hydroxyethyl cellulose has a viscosity of about 4500 cps to about 6500 cps (2% aqueous solution at 20° C.).

In embodiments, the composition comprises about 1 mg/mL to about 50 mg/mL of a viscosity modifying agent, e.g., about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, or about 50 mg/mL, including all values and ranges in between.

In embodiments, the composition comprises about 15 mg/mL of a viscosity modifying agent. In embodiments, the composition comprises about 10 mg/mL of a viscosity modifying agent. In embodiments, the composition comprises about 5 mg/mL of a viscosity modifying agent. In embodiments, the composition comprises about 2 mg/mL of a viscosity modifying agent. In embodiments, the composition comprises about 1 mg/mL of a viscosity modifying agent.

In embodiments, the composition comprises about 0.1% by weight to about 0.5% by weight of a viscosity modifying agent, e.g., about 0.1% by weight, about 0.2% by weight, about 0.3% by weight, about 0.4% by weight, or about 0.5% by weight, including all values and ranges in between. In embodiments, the composition comprises about 0.15% by weight of a viscosity modifying agent. In embodiments, the composition comprises about 0.10% by weight of a viscosity modifying agent. In embodiments, the composition comprises about 0.20% by weight of a viscosity modifying agent. In embodiments, the composition comprises about 0.5% by weight of a viscosity modifying agent.

In embodiments, the viscosity of the composition is about 1 to 2000 cps (or mPa-s). In embodiments, the viscosity of the composition is about 1 to 1000 cps, e.g., about 25 cps, about 50 cps, about 75 cps, about 100 cps, about 125 cps, about 150 cps, about 175 cps, about 200 cps, about 300 cps, about 400 cps, about 500 cps, about 600 cps, about 700 cps, about 800 cps, about 900 cps, or about 1000 cps, including all values and ranges there between. In embodiments, the viscosity of the composition is about 1 to 100 cps. In embodiments, the viscosity of the composition is about 1 to 50 cps. In embodiments, the viscosity of the composition is from about 1 to 2000 cps, wherein the viscosity is measured at 21° C. using a rotational viscosity method. In embodiments, the viscosity of the composition is from about 1 to 50 cps, wherein the viscosity is measured at 21° C. using a rotational viscosity method. In embodiments, the viscosity of the composition is from about 1 to 100 cps, wherein the viscosity is measured at 21° C. using a rotational viscosity method.

In embodiments, the viscosity of the composition is about 2000 cps. In embodiments, the viscosity of the composition is about 1800 cps. In embodiments, the viscosity of the composition is about 1600 cps. In embodiments, the viscosity of the composition is about 1500 cps. In embodiments, the viscosity of the composition is about 1400 cps. In embodiments, the viscosity of the composition is about 1200 cps. In embodiments, the viscosity of the composition is about 1000 cps. In embodiments, the viscosity of the composition is about 800 cps. In embodiments, the viscosity of the composition is about 600 cps. In embodiments, the viscosity of the composition is about 400 cps. In embodiments, the viscosity of the composition is about 300 cps. In embodiments, the viscosity of the composition is about 200 cps. In embodiments, the viscosity of the composition is about 100 cps. In embodiments, the viscosity of the composition is about 100 cps. In embodiments, the viscosity of the composition is about 90 cps. In embodiments, the viscosity of the composition is about 80 cps. In embodiments, the viscosity of the composition is about 70 cps. In embodiments, the viscosity of the composition is about 60 cps. In embodiments, the viscosity of the composition is about 50 cps. In embodiments, the viscosity of the composition is about 40 cps. In embodiments, the viscosity of the composition is about 20 cps. In embodiments, the viscosity of the composition is about 10 cps.

In embodiments, the viscosity of the composition is about 200 cps or less, 150 cps or less, 100 cps or less, 80 cps or less, 50 cps or less, or 25 cps or less. In embodiments, the viscosity of the composition is about 100 cps or less. In embodiments, the viscosity of the composition is about 50 cps or less.

The viscosity of the TXA composition is measured using methods known in the art, such as use of a viscometer or rheometer. In embodiments, the viscosity of the TXA composition is measured using a rotational viscosity method. One of ordinary skill in the art will recognize that factors such as temperature and shear rate may affect viscosity measurement. In embodiments, the viscosity of the composition of the present disclosure is measured at 20° C. +/−1° C. using a Brookfield LV/RV DV-II Viscometer, Brookfield Cone and Plate Viscometer Model VDV-III Ultra$^+$ with a CP40, or equivalent Spindle with a shear rate of approximately 22.50+/− approximately 10 (1/sec), or a Brookfield Viscometer Model LVDV-E with a SC4-18 or equivalent Spindle with a shear rate of approximately 26+/− approximately 10 (1/sec)). In embodiments, the viscosity of the composition of the present disclosure is measured according to a protocol described in USP <912>. In embodiments, the viscosity of the TXA composition of the disclosure is measured at 20° C. +/−5° C. In embodiments, the viscosity of the TXA composition is measured at 21° C. In other embodiments, the viscosity of the TXA composition is measured when the viscosity modifying agent is slowly added to achieve about 1 to 1000 cps at 20° C. +/−1° C. using a rotational viscosity method.

In embodiments, compositions of the present disclosure further comprise a stabilizing agent. In embodiments, the stabilizing agents is sodium citrate (all forms, 0.01 to 20% by weight), sodium pyrophosphate (0.1 to 10% by weight), EDTA (all forms, 0.01 to 20%), pentetate (all forms, 0.01 to 20%), or sodium glyconate (0.1 to 10% weight/volume) or a mixture thereof. The stabilizing agent should be used in an amount sufficient to increase the stability of the composition.

In embodiments, the amount of stabilizing agent used provides a stable composition showing no evidence of precipitation or sedimentation for at least about 24 hours after the composition formation.

In embodiments, the compositions of the present disclosure are stable following subjecting the composition to temperatures of about 10 to 40° C. for at least about 1-4 hours. In embodiments, the composition is stable following subjecting the composition to temperatures of about 30° C. for at least about 2 hours. In embodiments, the composition is stable following subjecting the composition to temperatures of about 121° C. for at least about 30 minutes. In embodiments, the composition has a shelf-life of about 1 year at about 25° C. In embodiments, the composition has a shelf-life of about 2 years at about 25° C. In embodiments, the composition has a shelf-life of about 6 months at about 40° C.

In embodiments, the compositions of the present disclosure are stable following subjecting the composition to ICH accelerated stability storage conditions. In embodiments, the compositions of the present disclosure are stable for at least one month at 40° C. (±2°) and 75% relative humidity (±5%). In embodiments, the compositions of the present disclosure are stable for at least three months at 40° C. (±2°) and 75% relative humidity (±5%). In embodiments, the compositions of the present disclosure are stable for at least six months at 40° C. (±2°) and 75% relative humidity (±5%).

In embodiments, the composition has a residence time of about 5 to 120 minutes following application to a bleeding wound. In embodiments, the composition has a residence time of about 10 to 60 minutes following application to a bleeding wound. In embodiments, the composition has a residence time of about 1 hour or more, about 2 hours or more, about 4 hours or more, about 8 hours or more, about 16 hours or more, about 20 hours or more, or about 24 hours or more following application to a bleeding wound.

In embodiments, the compositions of the present disclosure are preservative free. Alternatively, in embodiments, the compositions of the present disclosure comprise a preservative. In embodiments, the preservative is quaternary ammonium compound (such as benzalkonium chloride, benzoxonium chloride). In embodiments, the preservative is alkyl-mercury salts of thiosalicylic acid (such as thiomersal, phenylmercuric nitrate, phenylmercuric acetate or phenylmercuric borate, sodium perborate), sodium chlorite, parabens (such as methylparaben or propylparaben), alcohols (such as chlorobutanol, benzyl alcohol or phenyl ethanol), guanidine derivatives (such as, chlorohexidine or polyhexamethylene biguanide), sodium perborate, sorbic acid. Where appropriate, a sufficient amount of preservative is added to the TXA composition to ensure protection against secondary contaminations during use caused by bacteria and fungi.

In embodiments, the topical aqueous composition of TXA is sterile. The composition is sterilized by aseptic filtration, autoclaving or gamma irradiation.

In embodiments, the TXA compositions comprise an isotonicity agent. In embodiments, the isotonicity agent is betadex sulfobutyl ether sodium, calcium chloride, dextrose, dimethyl-β-cyclodextrin, glycerin, hydroxyethyl-β-cyclodextrin, hydroxypropyl betadex, magnesium chloride, magnesium oxide, maltodextrin, mannitol, potassium chloride, sodium chloride or trimethyl-β-cyclodextrin, or a mixture thereof. In embodiments, the isotonicity agent is sodium chloride, potassium chloride, calcium chloride or magnesium chloride, or a mixture thereof.

In embodiments, the TXA compositions comprise a wetting agent. In embodiments, the wetting agent is an alcohol (such as ethanol), glyceryl monooleate, benzethonium chloride, docusate sodium, emulsifying wax BP, hypromellose, phospholipids, polyethylene alkyl ethers, sodium lauryl sulfate, tricaprylin, benzalkonium chloride, cetrimide, cetrimonium bromide, cetylpyridinium chloride, xanthan gum, alpha tocopherol, butylparaben, ethylparaben, methylparaben, potassium sorbate, propylparaben, sorbic acid, emulsifying wax USP, glyceryl laurate, myristyl alcohol, poloxamer, polyoxyethylene alkyl ethers, polyoxyethylene castor oil derivatives, polyoxyethylene sorbitan fatty-acid esters, polyoxyethylene stearates, polyoxyl 15 hydroxystearate, polyoxylglycerides, polysorbate 80, propylene glycol dilaurate, propylene glycol monolaurate, sorbitan esters, sucrose palmitate, sucrose stearate, tyloxapol, or vitamin E polyethylene glycol succinate, or a mixture thereof.

In embodiments, the TXA compositions comprise a pH buffer agent. In embodiments, the pH buffer agent is acetic acid, adipic acid, ammonia solution, ammonium phosphate, ammonium sulfate, arginine, asparagine, boric acid, calcium carbonate, calcium lactate, tribasic calcium phosphate, citric acid, dibasic potassium phosphate, dibasic sodium phosphate, diethanolamine, glycine, histidine, hydroxyethylpiperazine ethanesulfonic acid, lysine acetate, lysine hydrochloride, maleic acid, malic acid, meglumine, methionine, monobasic sodium phosphate, monoethanolamine, monosodium glutamate, phosphoric acid, potassium citrate, potassium metaphosphate, sodium acetate, sodium bicarbonate, sodium borate, sodium carbonate, sodium citrate, sodium lactate, triethanolamine, or tromethamine, or a mixture thereof.

In embodiments, the pH buffer agent is sodium citrate. In embodiments, the pH buffer agent is citric acid. In embodiments, the pH buffer agent is sodium citrate and citric acid. In embodiments, the citric acid is anhydrous. In embodiments, the sodium citrate is the dihydrate.

In embodiments, the composition comprises about 0.1 mg/mL to about 20 mg/mL sodium citrate, e.g., about 0.1 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20.0 mg/mL, including all values and ranges in between. In embodiments, the composition comprises about 10 mg/mL sodium citrate. In embodiments, the composition comprises about 12 mg/mL sodium citrate. In embodiments, the composition comprises about 12.6 mg/mL sodium citrate. In embodiments, the sodium citrate is the dihydrate.

In embodiments, the composition comprises about 1 mg/mL to about 20 mg/mL citric acid, e.g., about 1.0 mg/mL, about 2.0 mg/mL, about 3.0 mg/mL, about 4.0 mg/mL, about 5.0 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, or about 20.0 mg/mL, including all values and ranges in between. In embodiments, the composition comprises about 10 mg/mL citric acid. In embodiments, the composition comprises about 10.15 mg/mL citric acid.

In embodiments, the TXA compositions comprise a pH adjusting agent. In embodiments, the pH adjusting agent is sodium hydroxide, hydrochloric acid, aqueous ammonia, diethanolamine, meglumine, sodium citrate, acetic acid, adipic acid, ammonium chloride, ascorbic acid, citric acid, fumaric acid, gluconolactone, lactic acid, maleic acid, malic acid, monobasic sodium phosphate, phosphoric acid, propionic acid, sulfuric acid, tartaric acid, calcium hydroxide, monoethanolamine, potassium bicarbonate, potassium citrate, potassium hydroxide, sodium bicarbonate, sodium borate, sodium carbonate, triethanolamine, or tromethamine, or a mixture thereof. In embodiments, the pH adjusting agent is hydrochloric acid. In embodiments, the pH adjusting agent is sodium hydroxide.

In embodiments, the compositions of the present disclosure have a pH of about 4.0 to about 8.0. In embodiments, the compositions of the present disclosure have a pH of about 4.0 to about 7.5, e.g., about 4.0 to about 7.0, about 4.0 to about 6.5, about 4.0 to about 6.0, about 4.0 to about 5.5, about 4.0 to about 5.0, about 4.0 to about 4.5, including any values or ranges therebetween. In embodiments, the compositions of the present disclosure have a pH of about 3.0 to about 5.0. In embodiments, the compositions of the present disclosure have a pH of about 4.0.

The compositions of the present disclosure are generally aqueous solutions. However, in embodiments, the compositions of the present disclosure are suspensions, viscous or semi-viscous gels, or other types of solid or semi-solid compositions, or those appropriate for sustained release. In embodiments, the pharmaceutical compositions of the present disclosure are formulated as solutions, ointments, sustained release formulation, and other dosage forms for topical administration or for sustained release delivery. Nonlimiting examples of the pharmaceutically acceptable vehicle or excipient or carrier are ointments, creams, liniments, pastes, patches, lotions, gels, shampoos, hydrogels, liposomes, sprays, aerosols, solutions, sponges, films, plasters, surgical dressings, bandages, or emulsions.

In embodiments, the compositions of the present disclosure further comprise an additional drug that would be desirable to deliver to the patient experiencing bleeding, particularly an epistaxis (nosebleed), preparatory to or as part of treatment of the epistaxis. In embodiments, the additional drug is a vasoconstrictor (e.g., epinephrine), antibiotic, antiseptic (e.g., chlorhexidine), anti-fungal, antiviral, analgesic, local anesthetic (lidocaine, xylocaine, etc.), non-steroidal anti-inflammatory drug, opioid, or anti-neoplastic.

A vasoconstrictor is useful to help bleeding vessels constrict prior to administration of a hemostatic medication such as an antifibrinolytic, and may desirably be delivered to the nasal tissue at or around the site of the bleeding before, during, and/or after application to the nasal tissue. In embodiments, the vasoconstrictor is phenylephrine, oxymetazoline (Afrin), or epinephrine. In embodiments, the vasoconstrictor is epinephrine.

In embodiments, the composition comprises TXA at a concentration of about 200 mg/mL to about 300 mg/mL and hydroxyethyl cellulose. In embodiments, the composition comprises TXA at a concentration of about 200 mg/mL to about 300 mg/mL and 0.5 mg/mL to about 2.5 mg/mL of hydroxyethyl cellulose. In embodiments, the composition comprises TXA at a concentration of about 200 mg/mL to about 300 mg/mL, sodium citrate dihydrate, citric acid, and hydroxymethyl cellulose. In embodiments, the composition is Formulation A, Formulation B, Formulation C, and Formulation D, as described in Table 1.

Topical Applicator for TXA Compositions

In one aspect, the present disclosure provides a topical applicator, wherein the applicator is saturated with topical aqueous compositions of the present disclosure (e.g., Formulation A, Formulation B, Formulation C, and Formulation 1:30 as described in Table 1). In embodiments, the use of any topical applicators known in the art, with or without some type of reservoir for the compositions, may also be contemplated. In embodiments, the topical applicator is an applicator described in International Application No. PCT/US2021/046745, the contents of which is hereby incorporated by reference in its entirety.

In embodiments, the topical applicator is a pad. In embodiments, the topical applicator pad is saturated with the TXA compositions of the present disclosure about 5% to about 100% of the pad volume. In embodiments, the topical applicator pad is saturated with about 10% to about 90% of the pad volume. In embodiments, the topical applicator pad is saturated with about 20% to about 80% of the pad volume. In embodiments, the topical applicator pad is saturated with about 30% to about 70% of the pad volume. In embodiments, the topical applicator pad is saturated with about 40% to about 60% of the pad volume. In embodiments, the topical applicator pad is saturated with about 50% to about 55% of the pad volume. In embodiments, the topical applicator pad is saturated with about 30% to about 70% of the pad volume.

Methods of Use

In one aspect, the present disclosure provides methods of using the compositions of TXA (e.g., Formulation A, Formulation B, Formulation C, and Formulation D as described in Table 1) for reducing bleeding. The present disclosure also provides methods of using the compositions of TXA for treating or preventing various skin abnormalities, including wound, scar, blemishes, dark spots or other skin discoloration such as melasma.

In one aspect, the present disclosure provides a method for treating wound comprising saturating a topical applicator pad with a composition of the present disclosure; and applying an effective amount of the composition to the wound. In embodiments, the bleeding includes both an external bleeding or an internal bleeding that sources from a lumen or space and exposes an external site for a topical administration.

In embodiments, the present disclosure provides a method of treating epistaxis (nosebleed), in which the method comprises saturating a topical applicator pad with a composition of the present disclosure; and applying an effective amount of the composition to the patient's nose. In embodiments, the method of treating epistaxis (nosebleed) comprises administering about 1,000 mg to about 2,000 mg of tranexamic acid to the nose of a patient in one or both nostrils in need thereof.

In one aspect, the present disclosure provides a method of using the composition of TXA for treating a patient wherein the patient has a propensity for increased bleeding. In embodiments, the patient is undergoing post-cardiac bypass, extracorporeal membrane oxygenation (ECMO), or hemodialysis. In embodiments, the patient is suffering from a bleeding disorder. In embodiments, the patient has hemophilia, kidney disease, liver disease, low platelets from medications, or cancer. In embodiments, the patient is undergoing a hemorrhagic drug treatment regimen, such as anticoagulants and/or antiplatelets.

In embodiments, the present disclosure provides a method of using the composition of TXA for treating hemoptysis in a patient in need thereof, the method comprising administering an effective amount of a composition of the present disclosure to lungs of a patient in need thereof. In embodiments, the composition is administered by nebulization.

In embodiments, the present disclosure provides a method of using the composition of TXA for treating hemoptysis hematemesis (vomiting blood), hematochezia (rectal bleeding), or hematuria, the method comprising administering an effective amount of a composition of the present disclosure to a patient in need thereof.

In embodiments, the present disclosure provides a method for treating abnormalities of the skin by administering an effective amount of a composition of the present disclosure. In embodiments, the method comprises saturating a topical applicator pad with the topical TXA composition; and applying an effective amount of the composition to the melasma.

In embodiments, the present disclosure provides a method for preventing scar or wound hyperpigmentation. In embodiments, the method comprises saturating a topical applicator pad with the TXA composition; and applying an effective amount of the composition to the area of scarring or hyperpigmentation.

In embodiments, the compositions of the present disclosure are topically administered to a subject suffering from bleeding as needed, once per day, twice per day, three times per day, or four times per day.

In embodiments, the compositions of the present disclosure are topically administered to a subject suffering from wound as needed, e.g., once per day, twice per day, or three times per day. In embodiments, the compositions of the present disclosure are topically administered to a subject suffering from skin abnormalities once per day, twice per day, three times per day, once per week, twice per week, three times per week, three times per week, five times per week, once every two weeks, one every three weeks, once per month, once every two months, once every three months, or once every six months. In embodiments, the compositions of the present disclosure are topically administered to a subject having cosmetic concerns once per day, twice per day, three times per day, once per week, twice per week, three times per week, five times per week, once every two weeks, one every three weeks, once per month, once every two months, once every three months, or once every six months.

NUMBERED EMBODIMENTS

1. A topical aqueous composition for reducing bleeding, comprising: tranexamic acid at a concentration of about 50-500 mg/mL in a pharmaceutically acceptable aqueous vehicle.
2. The composition of embodiment 1, wherein the concentration of tranexamic acid is about 200 mg/mL to about 300 mg/mL.
3. The topical composition of embodiment 1, wherein the tranexamic acid concentration is about 350 mg/mL.
4. The topical composition of any one of embodiments 1-3, wherein the composition is packaged in a suitable container.
5. The topical composition of any one of embodiments 4, wherein the volume of the composition is about 2-10 mL.
6. The topical composition of any one of embodiments 5, wherein the volume of the composition is about 5 mL.
7. The topical composition of any one of embodiments 4-6, wherein the packaged composition comprises about 250 mg to about 2,000 mg of tranexamic acid.
8. The topical composition of any one of embodiments 1-6, wherein the viscosity of the composition is about 1 to 2000 cps, measured at 21° C. using a rotational viscosity method.

9. The topical composition of embodiment 8, wherein the viscosity of the composition is about 50 cps or less or 100 cps or less, measured at 21° C. using a rotational viscosity method.

10. The topical composition of any one of embodiments 1-9, further comprising a viscosity modifying agent.

11. The topical composition of embodiment 10, wherein the viscosity modifying agent is selected from the group consisting of cellulose derivatives (e.g., methylcellulose, microcrystalline cellulose, and hydroxypropyl methylcellulose), gums (e.g., acacia, guar gum, tragacanth, and xanthan gum), polymers (e.g., polymers, polyvinylpyrrolidone), colloidal silicone dioxide and silicates.

12. The topical composition of embodiment 11, wherein the viscosity modifying agent is hydroxyethyl cellulose.

13. The topical composition of any one of embodiments 1-12, further comprising a pH buffer agent.

14. The topical composition of embodiment 13, wherein the pH buffer agent is sodium citrate and citric acid.

15. The topical composition of any one of embodiments 1-14, wherein the pH of the composition is about 3 to 5.

16. The topical composition of embodiment 15, wherein the pH of the composition is about 4.

17. The topical composition of any one of embodiments 1-16, wherein the composition is stable following subjecting the composition to temperatures of about 30° C. for at least about 2 hours.

18. The topical composition of any one of embodiments 1-17, wherein the composition is sterile.

19. The topical composition of any one of embodiments 1-18, wherein the composition is sterilized by aseptic filtration or autoclaving.

20. The topical composition of any one of embodiments 1-19, further comprising a vasoconstrictor (e.g., epinephrine, phenylephrine), local anesthetic (lidocaine, xylocaine etc.), antibiotic, anti septic (e.g., chl orhexi di ne), anti-fungal, antiviral, analgesic, non-steroidal anti-inflammatory drug, opioid, chemotherapeutic, biologic, monoclonal antibody or other anti-neoplastic agent.

21. A topical applicator pad saturated with the topical composition of any one of embodiments 1-20.

22. The topical applicator pad of embodiment 21, wherein about 30% to about 70% of the pad volume is saturated with the composition.

23. A method of reducing bleeding in a wound comprising:
saturating a topical applicator pad with the topical composition of any one of embodiments 1-20, and administering an effective amount of the composition to the wound.

24. A method of treating epistaxis, the method comprising: saturating a topical applicator pad with the topical composition of any one of embodiments 1-20, and administering an effective amount of the composition to the nose of a patient in need thereof.

25. A method of treating melasma, the method comprising:
saturating a topical applicator pad with the topical composition of any one of embodiments 1-20, and administering an effective amount of the composition to the melasma.

26. A method of preventing scar or wound hyperpigmentation, the method comprising:
saturating a topical applicator pad with the topical composition of any one of embodiments 1-20, and administering an effective amount of the composition to the wound area.

27. A method of treating hemoptysis, the method comprising:
administering an effective amount of the composition of any one of embodiments 1-20 to lungs of a patient in need thereof.

28. The method of embodiment 27, wherein the composition is administered by nebulization.

EXAMPLES

The present invention is further illustrated by reference to the following Examples. However, it is noted that these Examples, like the embodiments described above, are illustrative and are not to be construed as restricting the scope of the invention in any way.

Example 1. Preparation of TXA Formulations

Exemplary viscosity-modified formulations of the Tranexamic Acid (TXA) having concentrations of TXA of from 200 mg/mL to 300 mg/mL and a viscosity modifying agent were prepared.

Under the tested conditions, the following viscosity modifying agents provided compositions that were not suitable for further pharmaceutical development: Carbomers (Carbopol 981 and 5984), Xanthan gum, Poloxamer 407, carboxymethyl cellulose (low, medium and high viscosity), Methylcellulose 400 cP and Pemulen TR-1 and TR2. For example, the compositions were physically unstable (phase separation) at higher temperatures (such as at 40° C., or autoclave conditions (121° C. for about 25 min)) or provided unsuitable composition viscosity.

In contrast, and unexpectedly, the use of hydroxyethyl cellulose as the viscosity modifying agent provided compositions suitable for further pharmaceutical development (e.g., suitable physical stability and viscosity). Thus, Formulations A-D listed in Table 1 (containing 200 mg/mL or 300 mg/mL TXA and hydroxyethyl cellulose) were prepared and found to provide compositions suitable for further pharmaceutical development.

TABLE 1

TXA formulations

| Component | Formulation A mg/mL | Formulation B mg/mL | Formulation C mg/mL | Formulation D mg/mL |
| --- | --- | --- | --- | --- |
| Citric Acid Anhydrous | 10.15 | 10.15 | 10.15 | 10.15 |
| Sodium Citrate Dihydrate | 12.6 | 12.6 | 12.6 | 12.6 |
| Tranexamic Acid | 200 | 300 | 200 | 300 |
| Hydroxyethyl cellulose (800-1500 cps) | 1.0 | 1.0 | 2.0 | 2.0 |
| Water for Injection (WFI) | Q.S. to 1.0 mL | Q.S. to 1.0 mL | Q.S. to 1.0 mL | Q.S. to 1.0 mL |

TABLE 1-continued

TXA formulations

| Component | Formulation A mg/mL | Formulation B mg/mL | Formulation C mg/mL | Formulation D mg/mL |
|---|---|---|---|---|
| Hydrochloric Acid | HCl, 6M: as needed. Adjust pH to pH 4.0 | | | |
| Sodium Hydroxide | | | | |

Q.S.: a sufficient quantity

Method of making: Citric acid anhydrous was dissolved in water and mixed for at least 5 minutes. Sodium citrate dihydrate was added to the solution and mixed for at least 5 minutes, followed by an initial pH measurement. To the resulting solution, TXA was added and mixed for 5 minutes. The pH of the solution was then adjusted to pH 4.0±0.1 with 6M HCl. The resulting solution was mixed for additional 10 minutes. Hydroxyethyl cellulose (800-1500 cps) was then slowly added to the solution and mixed vigorously for at least 30 minutes. Water for injection (WFI) was added continuously and mixed for at least 30 minutes to make the final TXA formulation. The viscosity of the formulation product was measured at 21° C. using a rotational viscosity method.

The invention claimed is:

1. A topical aqueous composition for reducing bleeding, comprising:
   tranexamic acid at a concentration of about 200 mg/mL to about 350 mg/mL and hydroxyethyl cellulose,
   wherein the topical composition has a viscosity of about 1 to 50 cps, measured at 21° C. using a rotational viscosity method, the hydroxyethyl cellulose has a viscosity of about 800 cps to about 6500 cps as determined in a 2% aqueous solution of the hydroxyethyl cellulose at 20° C., and the topical composition has a pH of about 3 to 5.

2. The topical composition of claim 1, wherein the concentration of tranexamic acid is about 200 mg/mL.

3. The topical composition of claim 1, wherein the concentration of tranexamic acid is about 300 mg/mL.

4. The topical composition of claim 1, wherein the hydroxyethyl cellulose has a concentration of about 1 mg/mL to about 2 mg/mL.

5. The topical composition of claim 1, wherein the hydroxyethyl cellulose has a viscosity of about 800 cps to about 1500 cps as determined in a 2% aqueous solution of the hydroxyethyl cellulose at 20° C.

6. The topical composition of claim 1, wherein the hydroxyethyl cellulose has a viscosity of about 4500 cps to about 6500 cps as determined in a 2% aqueous solution of the hydroxyethyl cellulose at 20° C.

7. The topical composition of claim 1, further comprising a pH buffer agent.

8. The topical composition of claim 7, wherein the pH buffer agent is sodium citrate and citric acid.

9. The topical composition of claim 1, wherein the pH of the composition is about 4.

10. The topical composition of claim 1, wherein the composition comprises: tranexamic acid at a concentration of about 200 mg/mL to about 300 mg/mL, hydroxyethyl cellulose, and a pH buffer agent, wherein the pH of the composition is about 4.

11. The topical composition of claim 1, wherein the composition comprises: tranexamic acid at a concentration of about 200 mg/mL, hydroxyethyl cellulose, and a pH buffer agent, wherein the pH of the composition is about 4.

12. The topical composition of claim 1, wherein the composition comprises: tranexamic acid at a concentration of about 300 mg/mL, hydroxyethyl cellulose, and a pH buffer agent, wherein the pH of the composition is about 4.

13. The topical composition of claim 1, wherein the concentration of tranexamic acid is about 200 mg/mL, and the pH of the composition is about 4.

14. The topical composition of claim 1, wherein the concentration of tranexamic acid is about 300 mg/mL, and the pH of the composition is about 4.

15. The topical composition of claim 1, wherein the composition is sterile.

16. The topical composition of claim 15, wherein the composition is sterilized by aseptic filtration or autoclaving.

17. A kit, comprising: the topical composition of claim 1 packaged in a container.

18. The kit of claim 17, wherein the packaged composition comprises about 250 mg to about 2,000 mg of tranexamic acid.

19. The kit of claim 17, wherein the composition in the container has a volume of about 0.5 mL to about 20 mL.

20. The topical composition of claim 1, wherein the concentration of tranexamic acid is about 250 mg/mL, and the pH of the composition is about 4.

21. The topical composition of claim 1, wherein the composition comprises:
   tranexamic acid at a concentration of about 250 mg/mL, hydroxyethyl cellulose, and a pH buffer agent, wherein the pH of the composition is about 4.

22. A sterile topical aqueous composition for reducing bleeding, comprising:
   tranexamic acid at a concentration of about 200 mg/mL to about 350 mg/mL, hydroxyethyl cellulose having a viscosity of about 800 cps to about 6500 cps as determined in a 2% aqueous solution of the hydroxyethyl cellulose at 20° C.,
   and a pH buffer agent,
   wherein the topical composition has a viscosity of about 1 to 50 cps and the topical composition has a pH of about 3 to 5.

23. The sterile topical aqueous composition of claim 22, wherein the concentration of tranexamic acid is about 200 mg/mL to about 300 mg/mL.

24. The sterile topical aqueous composition of claim 22, wherein the concentration of tranexamic acid is about 250 mg/mL.

25. The sterile topical aqueous composition of claim 22, wherein the pH of the composition is about 4.

* * * * *